United States Patent [19]
McAleer et al.

[11] Patent Number: 5,814,205
[45] Date of Patent: Sep. 29, 1998

[54] DETECTION OF LEAD IN BLOOD

[75] Inventors: Jerome Francis McAleer; Martin Robert Ackland, both of Wantage; Elliot Verne Plotkin, Inverness; Lucinda Cordeiro, Bray-on-Thames, all of United Kingdom

[73] Assignee: Palintest Limited, Tyne & Wear, United Kingdom

[21] Appl. No.: 693,210

[22] PCT Filed: Feb. 10, 1995

[86] PCT No.: PCT/GB95/00269

§ 371 Date: Oct. 15, 1996

§ 102(e) Date: Oct. 15, 1996

[87] PCT Pub. No.: WO95/22052

PCT Pub. Date: Aug. 17, 1995

[30] Foreign Application Priority Data

Feb. 11, 1994 [GB] United Kingdom ............ 9402661

[51] Int. Cl.⁶ ........................................... G01N 27/26
[52] U.S. Cl. .................. 205/789; 204/415; 204/418; 205/789.5; 205/792; 205/793; 422/82.03; 436/73; 436/74; 436/81; 436/83; 436/84; 436/808
[58] Field of Search .................. 204/403, 415, 204/418, 419; 436/73, 74, 79, 80, 81, 83, 84, 807, 808; 205/781.5, 789, 789.5, 790, 792, 793, 777.5, 778; 435/975; 422/82.03

[56] References Cited

U.S. PATENT DOCUMENTS

| 4,090,926 | 5/1978 | Matson | 204/1 T |
|---|---|---|---|
| 4,409,088 | 10/1983 | Kanno et al. | 204/402 |
| 4,929,313 | 5/1990 | Wrighton | 205/792 |
| 5,078,854 | 1/1992 | Burgess et al. | 204/403 |
| 5,217,594 | 6/1993 | Henkens et al. | 204/403 |
| 5,284,567 | 2/1994 | Matson | 204/403 |
| 5,368,707 | 11/1994 | Henkens et al. | 204/153.12 |
| 5,468,366 | 11/1995 | Wegner et al. | 436/74 |
| 5,512,489 | 4/1996 | Girault et al. | 205/777.5 |

FOREIGN PATENT DOCUMENTS

| 0 203 864 | 3/1986 | European Pat. Off. . |
| WO 91/08474 | 6/1991 | WIPO . |
| WO 91/11710 | 8/1991 | WIPO . |
| WO 93/16378 | 8/1993 | WIPO . |

*Primary Examiner*—Bruce F. Bell
*Attorney, Agent, or Firm*—Howson and Howson

[57] ABSTRACT

A device (10) is disclosed for measuring the concentration of metal ions in solution, particularly lead in blood. The device comprises a mercury free electrode (16), which is separated from the test solution (21) by a layer of material (20) which permits passage therethrough of the ions to be measured. In preferred embodiments an insulating layer (18) having an array of photoablated holes (19) is disposed between the electrode and the ion-permeable layer (20). Also disclosed are methods for operating the device and measuring ion concentration using anodic stripping voltametry, and assay kits incorporating devices as described together with appropriate meters and circuitry.

20 Claims, 4 Drawing Sheets

DETECTION OF LEAD IN BLOOD

This application is a 371 of PCT/GB95/00269 filed on Feb. 10, 1995.

FIELD OF THE INVENTION

This invention relates to devices and methods for measuring the quantity of metal ions in solution, particularly (but not exclusively) the measurement of lead in blood.

BACKGROUND TO THE INVENTION

It has been well known for many years that lead is a toxic element and can have a number of serious health effects. Young children are especially at risk from lead poisoning. They can be exposed to lead from sources such as water (lead pipes), food, and air (leaded petrol). Old paint can contain a high concentration of lead and the most common cause of lead poisoning in young children is from eating paint chippings or dust from the walls or windows of old houses.

In the United States of America the Center for Disease Control (CDC) considers lead poisoning such a serious problem that it recommends all children in the country under 6 years of age be screened for lead. The amount of lead which a child has been exposed to is determined by measuring the concentration of lead in the child's blood. Over the years, as more has been learned about the adverse effect of lead on children, the blood lead concentration considered safe has steadily declined. In 1985 the CDC considered a lead concentration of less than 25 $\mu$g/dl to be acceptable. In 1991 the CDC lowered the safe lead level to 10 $\mu$g/dl.

Until recently much of the screening for lead poisoning was done using a fluorometric method called the zinc protoporphyrin test. This method is quick and cheap but is not accurate or sensitive enough for measuring lead at the new lower limit of 10 $\mu$g/dl.

Atomic absorption spectroscopy (AA) can be used to measure lead in blood very accurately at low concentrations but the method is not practicable for screening because the instrument is large, very expensive, and requires a highly trained operator.

The electrochemical method of anodic stripping voltametry (ASV) is another way of measuring lead in blood. In ASV, an electrode in contact with a solution to be tested is held at a negative potential for a sufficient period of time to reduce metal ions in the solution and concentrate them at the electrode. The potential is then ramped or scanned in the positive direction and any metals present will be stripped from the electrode when the unique oxidation potential of the respective metal is reached. The current produced during the stripping of each metal is proportional to the concentration of that metal in the test solution. Commercial ASV instruments are available but they are large, expensive, and not particularly accurate when used for measuring low concentrations of lead in blood.

The CDC is now actively encouraging development of a system which is small, portable, cheap, and easy to use, but can measure low concentrations of lead in blood with good accuracy and precision. At the present time there are no commercially available systems which meet these criteria, but this invention relates to a system which shows promise of meeting the required criteria.

SUMMARY OF THE INVENTION

In one aspect, the invention provides a device for measuring the quantity of ions of a predetermined metallic element which are present in a solution, the device comprising a mercury-free electrode separated from the solution by a layer of material which permits passage therethrough of the ions to be measured.

A preferred embodiment of the new system, designed for measuring lead in blood, uses a small, portable meter into which safely disposable cheap electrode strips are placed. A small volume of blood is added to a tube containing acid. This is mixed briefly to acidify the blood and release any bound lead. A drop of acidified blood is placed on the electrode strip and a button on the meter is pushed to start the analysis. In 2 or 3 minutes, the lead concentration in that sample of blood is displayed on the meter. A fresh electrode strip is used for each blood lead test, the used strips being disposable without environmental problems.

The improvements made possible by this invention are due to the use of mercury-free disposable electrode strips which have an ion exchange membrane covering the electrode from which the lead (or other metal) will be stripped. Conventional ASV equipment uses an electrode made from mercury or covered with mercury. The use of such an electrode has disadvantages because of the toxicity of mercury and the problems of its proper disposal. The electrodes used in a system according to this invention do not need to use mercury. The use of mercury-free disposable electrode strips opens the possibility of a rapid lead-in-blood test which is quick and simple to do. The invention eliminates the need for any cleaning, pre-plating, or preconditioning which is often necessary when conventional electrodes are used for ASV (although, as will be seen below, pre-plating electrodes according to the invention can have certain advantages).

When conventional electrodes are used for measuring lead in blood it is difficult to measure low lead concentration due to fouling of the electrode surface by proteins and other blood components. The membrane covering an electrode in a system according to this invention prevents this fouling and enables the required low lead levels in blood to be easily measured.

Devices according to the invention permit determination of lead-in-blood at levels below 25 $\mu$g/dl. A preferred device comprises a disposable mercury-free electrode strip having a substrate supporting a working microelectrode array adjacent to a reference electrode, a respective conductive path for each electrode leading to a connection end thereof for each said path, at least the microelectrode array being coated with an ion exchange membrane. Desirably the microelectrode array comprises a conducting layer (e.g. carbon) overlain by an electrically insulating layer, the insulating layer being laser photoablated to exhibit an array of small holes which expose the conducting layer underneath. Between 100 and 400 holes of some 40 micron diameter over a conducting area of some 5 mm by 3 mm have been found to be satisfactory. Preferably, the electrode is a disposable electrode.

The electrode strips used in our system preferably consist of a carbon working electrode and a silver/silver chloride reference electrode which are made by printing tracks of conductive ink onto a glass or plastics base. The preferred configuration of working electrode is a microelectrode array which gives a large signal to background ratio. Such an array can be made by printing an electrically insulating layer over the carbon working electrode. Laser photoablation is then used to make small holes in this insulating layer to expose the underlying carbon layer. The construction of a microelectrode array in this manner is described in WO91/08474.

To complete the strip an ion exchange membrane is formed over the working electrode.

Electrodes as described above work well at pH>2, but they are less sensitive under more acid conditions. A convenient way to overcome this limitation is to preplate the carbon electrode with silver before the ion exchange layer is applied. -The amount of silver plated onto the electrode is critical, since if insufficient silver is deposited lead sensitivity is diminished, whilst if too much silver is deposited a large oxygen reduction background is observed. We have found very good lead stripping peaks can be obtained by preplating the electrode at approximately −1.0 V versus silver chloride for between 5 and 600 seconds using a solution containing between 1 and 100 ppm of silver ions. Ideally, silver is plated for 60 seconds using a 10 ppm silver solution. These conditions appear to lead to an ideal distribution of silver nuclei on which lead nucleation can initiate. It is also envisaged that other noble metals such as rhodium, palladium and platinum may be used in place of silver. Furthermore, it is believed that pre-plating with silver or another noble metal in this way will enhance the low pH sensitivity of electrodes in general, and this feature of the invention is therefore not restricted to the use of mercury-free electrodes, or those containing ion-permeable layers.

A further convenient way to introduce silver is to incorporate a silver salt into a layer over the electrode. In this manner the silver is coplated with the target analyte during the test. A similar approach can be employed for electrodes which use mercury, in this case a mercury salt being incorporated into the layer. Alternatively, silver may be incorporated during the printing of the carbon electrode, by using an appropriate mixture of silver and carbon inks, or by printing carbon ink made from carbon particles metallized with silver.

An additional benefit of using silver is that its presence appears to discriminate against the deposition of copper. Copper is present in quite large quantities in human blood samples and can interfere with the lead determination, because the oxidation potential of copper is similar to that of lead. The problem of copper interference may also be addressed by causing the copper to be unavailable to the electrode by, for example, precipitating the copper with ferricyanide ($[Fe^{3+}(CN^-)_6]^{3-}$). The ferricyanide can be added to the sample during the pretreatment phase (for example by subjecting the sample to 1:10 dilution with a 5% potassium ferricyanide solution). Again, this aspect of the invention is not restricted to mercury-free electrodes, or those coated with an ion-permeable layer, and it is envisaged that the use of ferricyanide to remove copper ions will be of use with electrodes in general.

A further way in which the problems associated with copper deposition may be diminished is by the addition of a reagent which affects the relative oxidation potentials of copper and lead, so that the anodic stripping voltametry peaks therefor are separated from each other, and therefore readily distinguishable. We have found that a good effect may be achieved with potassium iodide, which can be added, for example, by diluting the sample 9:1 with 0.2M potassium iodide solution. As with the use of ferricyanide, the use of potassium iodide is thought to have general applicability in the avoidance of detection difficulties due to copper, and this aspect of the invention is therefore not limited to mercury-free electrodes or those having ion-permeable layers.

In another aspect, the invention extends to a method for determining the quantity of ions of a predetermined metallic element which are present in a solution, comprising the steps of contacting said solution with the layer of material overlying the mercury-free electrode, and determining the number of said ions coming into contact with said electrode by a voltametric method.

The invention provides in a further aspect an assay kit comprising a device as described and a meter for connection to said mercury-free electrode and to a reference electrode.

Suitably the meter is one into which the electrode strip can be inserted to put each connection end in electrical contact with a sensing circuit. Preferably, the sensing circuit is adapted to hold the microelectrode array at a negative potential relative to the reference electrode for a first period and then to apply a gradually increasing potential in the positive direction to the working electrode to strip lead from the microelectrode array when the oxidation potential for lead (or other metal under test) is reached.

Conveniently means is provided in the meter to assess the integral of current against time at the stripping voltage for lead to determine a peak area for the stripped lead, since this peak area is related to the concentration of lead in the sample of blood fed to the strip.

The assay kit can conveniently also include means to contain a blood sample while it is diluted with acid (e.g. HCl), a supply of acid for such dilutions and means to transfer a drop of acid-diluted blood to an electrode strip in the meter.

BRIEF DESCRIPTION OF THE DRAWINGS

The invention will now be further described, by way of example, with reference to the accompanying drawings, in which.

DETAILED DESCRIPTION OF THE PREFERRED EMBODIMENTS

Figure 1:
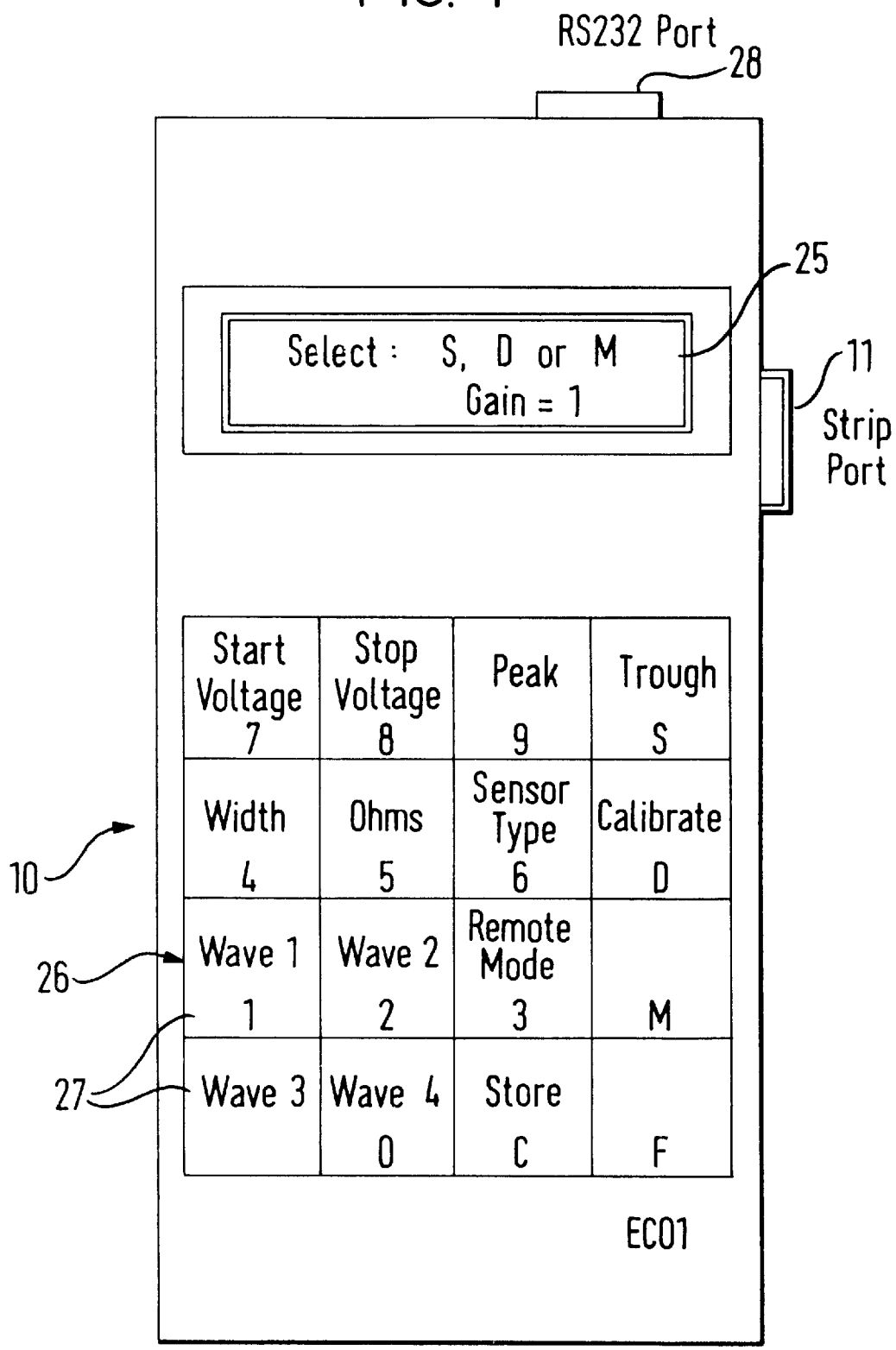
FIG. 1 is a schematic view of a meter unit for use in the determination of the concentration of lead in blood.
Figure 2:
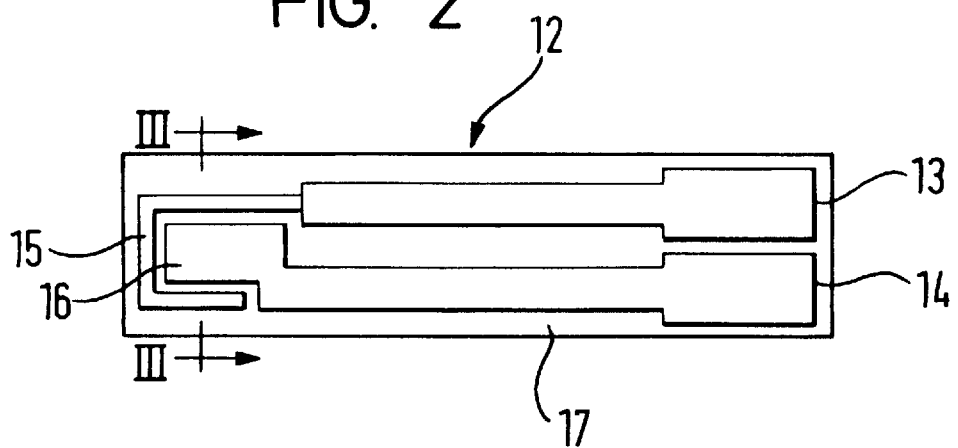
FIG. 2 is a plan view of a disposable micro-array sensing strip for plugging into the unit of FIG. 1.

The meter 10 shown in FIG. 1 (some 10 cm×20 cm×4 cm) has a socket 11 into which a sensing strip 12 shown in FIG. 2 can be inserted to put its contact areas 13, 14 in electrical connection with electronic circuitry within the meter.

The meter 10 also includes an alpha-numeric display screen 25 and a bank 26 of buttons 27 for controlling the electronic circuitry in the casing of the meter 10. The meter 10 also includes a port 28 for connection, if required, to a computer and VDU (not shown).

The strip 12 includes two printed carbon tracks, one leading from area 13 to a printed Ag/AgCl reference electrode 15 and the other leading from area 14 to a microelectrode array 16. The substrate can be a glass or plastics plate 17.

The array 16 comprises an electrically insulating layer 18 over the carbon track which has been provided with an array (e.g. 280–14×20) of small (e.g. 40 microns diameter) holes 19 spaced apart (e.g. 160 microns apart) over a small area as shown. The pattern of holes can be punched by photoablation as described in WO91/08474.

Overlying the open tops of the holes 19 is a layer 20 of a semipermeable ion exchange membrane. This may be manufactured for example from a perfluorosulphonated ion exchange resin (ionomer), such as NAFION (Trade Mark of Du Pont), or a poly(ester-sulphonic acid) film. In a practical embodiment the membrane was created from a dried drop (2 $\mu$l) of a 3% NAFION solution in 75% ethanol/25% water.

Figure 3:
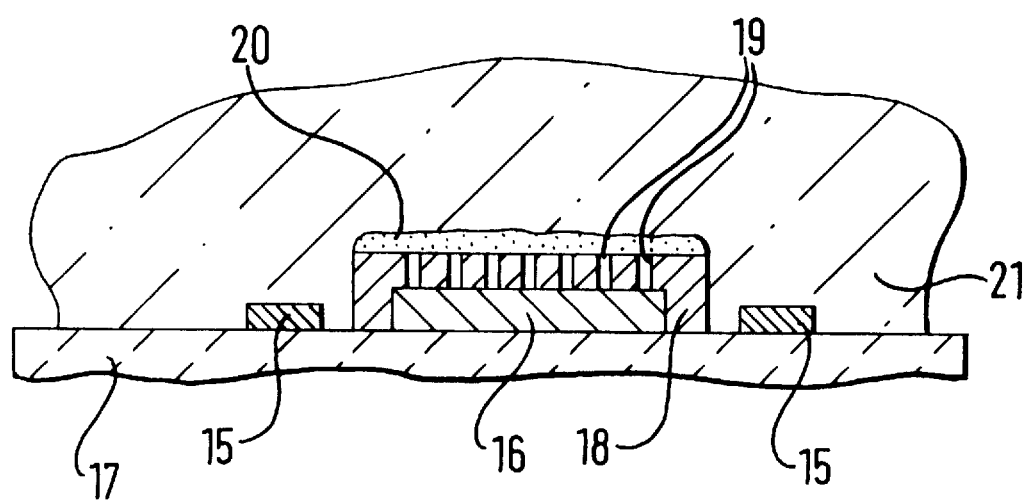
FIG. 3 is a schematic sectional view, on an enlarged scale, on the line iii—iii of FIG. 2.

FIG. 3 also shows a drop 21 of acid-diluted blood on which a lead concentration test is to be conducted.

The electronic circuitry within meter 10 first applies a negative potential to area 14 relative to area 13 for a period sufficient to reduce metal ions in the blood drop 21 applied to the strip 12 and concentrate them at the surface of the electrode 16 and then applies a ramped potential in the positive direction to strip metals from the electrode 16 when the specific oxidation potential of the metal in question is reached.

Figure 4:
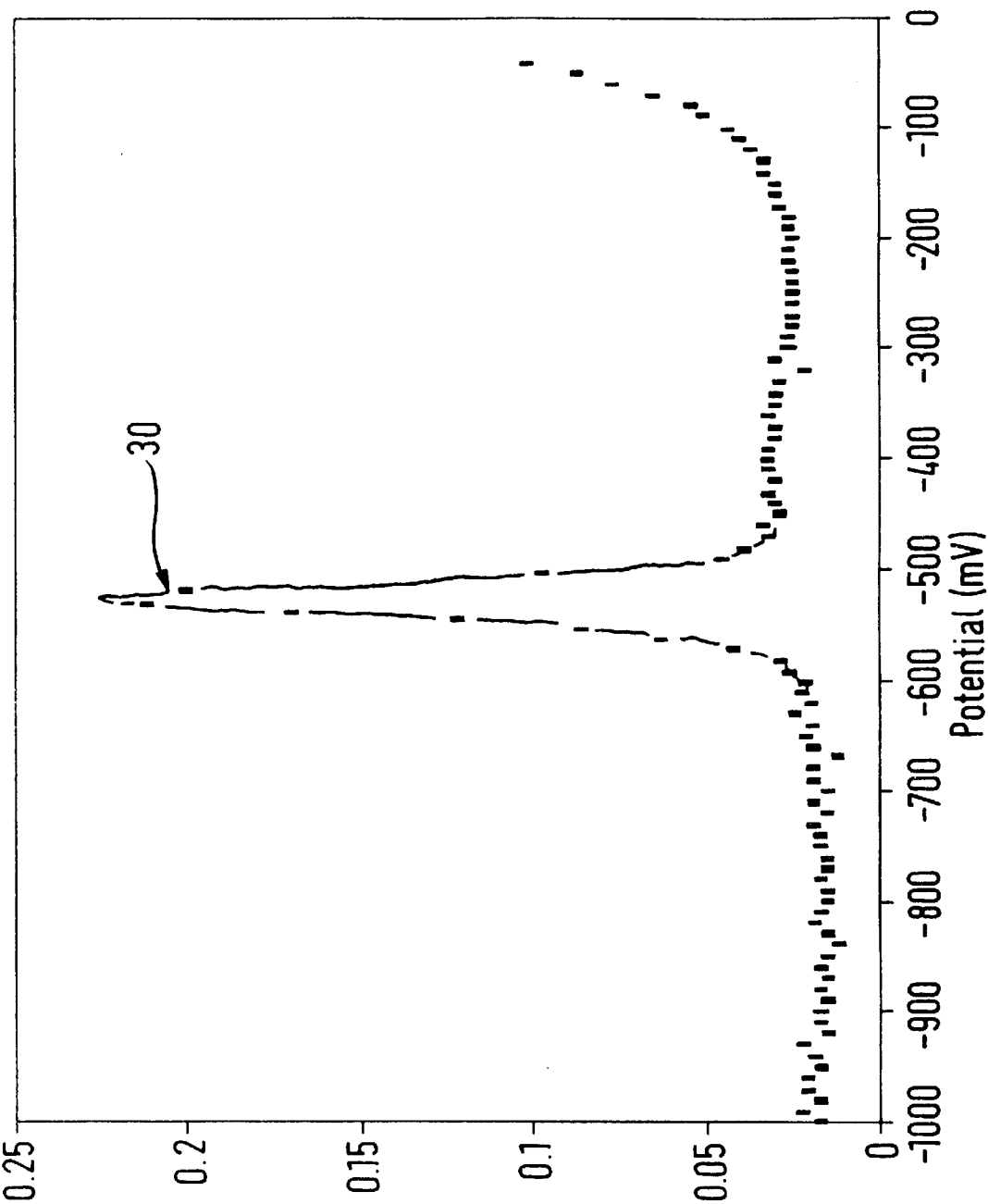
FIG. 4 is a typical ASV display of current versus stripping potential showing a peak due to a lead concentration in blood of 5 $\mu$g/dl.

FIG. 4 shows a typical plot of current flowing between electrodes 15 and 16 as the ramp voltage increases, the peak 30, occurring between −500 and −600 mV, representing the presence of lead.

The circuitry in the unit 10 can determine the area under the peak 30 and this can be displayed digitally on the screen 25 to give a measure of the concentration of lead in the blood sample 21.

Figure 5:
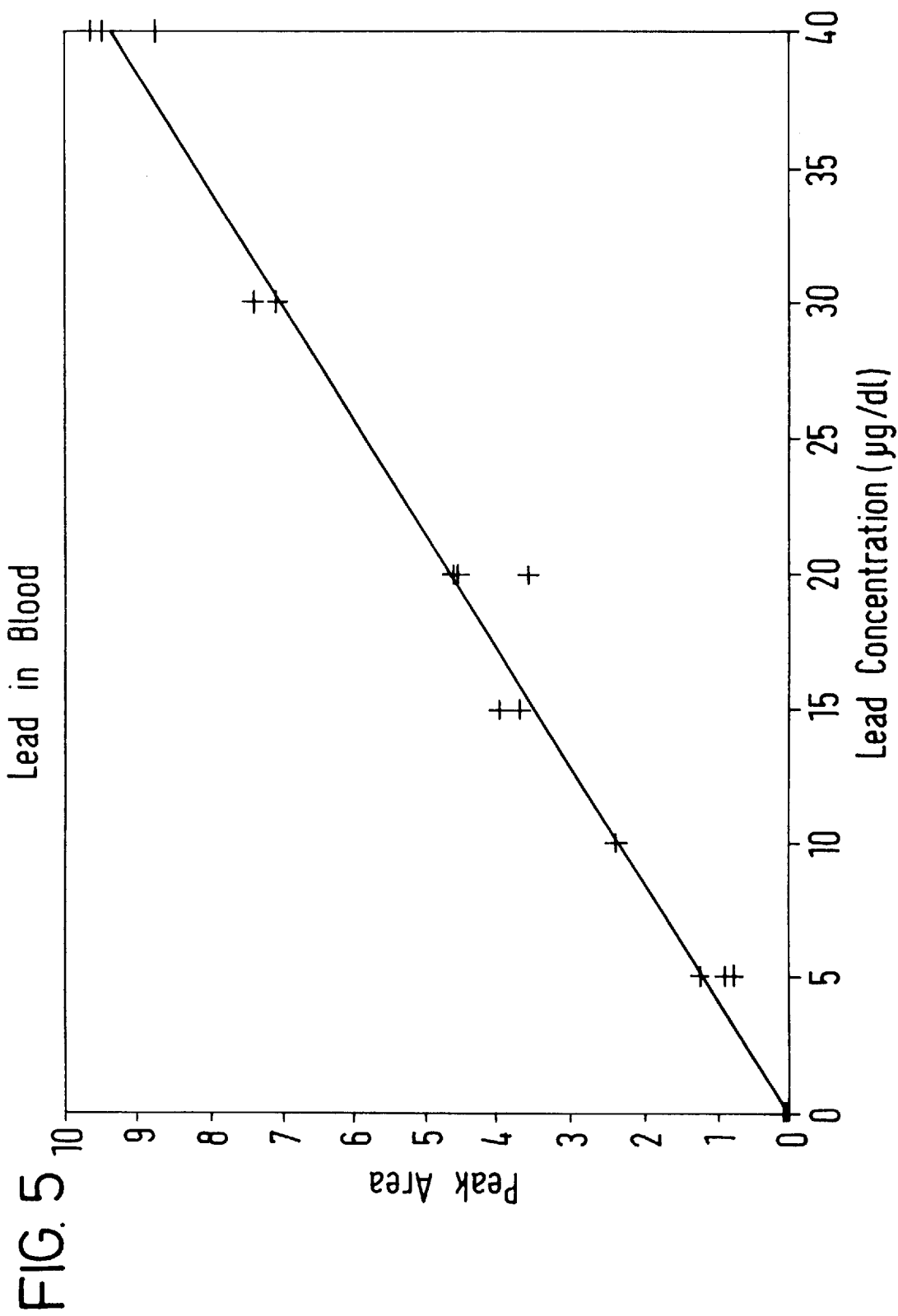
FIG. 5 is a graph showing test results expressed as peak areas for various concentrations of lead-in-blood.

To check the accuracy of the meter 10, tests were conducted with samples of lead-free venous blood deliberately contaminated with 5, 10, 15, 20, 30 and 40 micrograms of lead per deciliter. The blood samples were each added to dilute HCl in a 1:3 ratio and drops of acidified blood were tested on separate strips 12. The peak area values secured were plotted as crosses on the graph of FIG. 5. It will be noted that a good approximation to a linear relationship between peak area and lead concentration is obtained.

Although we expect microelectrode areas faced by ion permeable layers will perform best in a system according to this invention it is expected that a lead-in-blood sensor capable of operating below the CDC safe lead level can be produced using a strip 12 much as shown in FIG. 2 but without the layer 18 or holes 19, the membrane 20 simply directly overlying the carbon area 16.

We claim:

1. A device for measuring the quantity of ions of a heavy metallic element which are present in a solution, the device comprising a mercury-free, carbon electrode to the surface of which a layer of silver is applied, said electrode being separated from the solution by means, comprising a layer of material, for preventing passage of macromolecules and other contaminants which would otherwise tend to foul the electrode, but permitting passage therethrough of the ions to be measured.

2. A device according to claim 1, wherein the layer of material for preventing passage of macromolecules and other contaminants is a membrane of perfluorosulphonated ion exchange resin.

3. A device according to claim 1, wherein the electrode comprises a printed track of conductive ink on an insulating base.

4. A device according to claim 1, wherein the electrode is a microelectrode.

5. A device according to claim 4, wherein the electrode is a disposable electrode.

6. A device according to claim 5, wherein a layer of insulating material is disposed between the electrode and the material for preventing passage of macromolecules and other contaminants, the layer of insulating material having an array of microholes formed therein.

7. A method for determining the quantity of ions of a heavy metallic element which are present in a solution, comprising the steps of contacting said solution with the layer of material for preventing passage of macromolecules and other contaminants overlaying the mercury-free carbon electrode of a device according to claim 1, and determining the number of said ions coming into contact with said electrode by a voltametric method.

8. A method according to claim 7, wherein the voltametric method used is anodic stripping voltametry.

9. A method according to claim 7, wherein the solution is acidified prior to testing.

10. A method according to claim 9, wherein a ferricyanide is added to the solution prior to testing to prevent any copper ions in the solution being deposited at the electrode.

11. A method according to claim 9, wherein a reagent is added to the solution prior to testing, the reagent serving to affect the relative oxidation potentials of copper and lead, so that the anodic stripping voltametry peaks for copper and lead are separated from each other.

12. A method according to claim 9, wherein said heavy metallic element is lead.

13. A method according to claim 7, wherein said heavy metallic element is lead, and said solution consists essentially of blood.

14. An assay kit comprising a device according to claim 1, and a meter for connection to said mercury-free carbon electrode and to a reference electrode.

15. An assay kit according to claim 14, in which the meter receives the said device in such a manner that the mercury-free carbon electrode and reference electrode are in electrical contact with a sensing circuit, the sensing circuit holding the mercury-free electrode at a negative potential relative to the reference electrode for a time sufficient for metal ions under test to be plated onto said mercury-free electrode, and thereafter gradually to increase the potential of the mercury-free electrode in the positive direction, said plated metal being stripped from said electrode when its characteristic oxidation potential is reached.

16. An assay kit according to claim 15, further comprising means for assessing the integral of current against time at the stripping voltage of the metal under test, thus to determine the area of the current peak and to give an indication of the concentration of said metal ions in said solution.

17. A device for measuring the quantity of ions of a heavy metallic element which are present in a solution, the device comprising a carbon electrode to the surface of which a layer of a silver salt is applied, such that a layer of metal is plated onto the electrode by reduction of the metal ions in the silver salt when said electrode is held at a negative potential in use, said electrode being separated from the solution by means, comprising a layer of material, for preventing passage of macromolecules and other contaminants which would otherwise tend to foul the electrode, but permitting passage therethrough of the ions to be measured.

18. A device according to claim 17, wherein the layer of material for preventing passage of macromolecules and other contaminants is a membrane of perfluorosulphonated ion exchange resin.

19. A device according to claim 17, wherein the electrode comprises a printed track of conductive ink on an insulating base.

20. A device according to claim 17, wherein the electrode is a microelectrode.

\* \* \* \* \*